US010184153B2

(12) United States Patent
Clelland et al.

(10) Patent No.: US 10,184,153 B2
(45) Date of Patent: Jan. 22, 2019

(54) SYSTEM AND METHOD FOR DIAGNOSIS AND TREATMENT OF NEUROPSYCHIATRIC DISORDERS

(71) Applicant: The Research Foundation For Mental Hygiene, Inc., Menands, NY (US)

(72) Inventors: James D. Clelland, New York, NY (US); Catherine L. Clelland, New York, NY (US)

(73) Assignee: The Research Foundation For Mental Hygiene, Inc., Menands, NY (US)

( * ) Notice: Subject to any disclaimer, the term of this patent is extended or adjusted under 35 U.S.C. 154(b) by 70 days.

(21) Appl. No.: 15/332,390

(22) Filed: Oct. 24, 2016

(65) Prior Publication Data

US 2017/0037477 A1 Feb. 9, 2017

Related U.S. Application Data

(63) Continuation of application No. 14/069,847, filed on Nov. 1, 2013, now abandoned, which is a continuation of application No. 13/323,413, filed on Dec. 12, 2011, now abandoned, which is a continuation of application No. 11/873,971, filed on Oct. 17, 2007, now Pat. No. 8,076,075.

(60) Provisional application No. 60/829,856, filed on Oct. 17, 2006.

(51) Int. Cl.
| | |
|---|---|
| *C12Q 1/6883* | (2018.01) |
| *G01N 33/50* | (2006.01) |
| *C12Q 1/68* | (2018.01) |
| *C12P 19/34* | (2006.01) |
| *A61K 31/7052* | (2006.01) |
| *A61K 33/00* | (2006.01) |
| *A61K 45/06* | (2006.01) |
| *A61K 31/519* | (2006.01) |
| *A61K 33/14* | (2006.01) |
| *A61K 31/5415* | (2006.01) |

(52) U.S. Cl.
CPC .......... *C12Q 1/6883* (2013.01); *A61K 31/519* (2013.01); *A61K 31/5415* (2013.01); *A61K 31/7052* (2013.01); *A61K 33/00* (2013.01); *A61K 33/14* (2013.01); *A61K 45/06* (2013.01); *C12Q 1/68* (2013.01); *G01N 33/50* (2013.01); *C12Q 2600/118* (2013.01); *C12Q 2600/156* (2013.01); *C12Q 2600/158* (2013.01); *G01N 2800/302* (2013.01); *G01N 2800/50* (2013.01)

(58) Field of Classification Search
None
See application file for complete search history.

(56) References Cited

PUBLICATIONS

Richardson (Neuropsychobiology, 2005, 52, 190-201).*
Furukawa (Ann Neurol, 1998, 44, pp. 10-16).*
Edelstein et al, J. Gene Med. vol. 6, pp. 597-602, 2004.*
Verma and Weitzman, Gene Therapy: Twenty-first century medicine. Annual Review of Biochemistry, vol. 74, pp. 711-738, 2005.*
Luo et al (Nature Biotechnology, vol. 18, pp. 33-37, 2000).*
Verma et al (Nature, vol. 389, pp. 239-242, 1997; e.g. p. 239, paragraph 1).*
Palù et al (J. Biotechnol. vol. 68, pp. 1-13, 1999.*
Ionnidis (Plost Med, 2005, 2(8):e124).*
Hegele, Arterioscler. Thromb. Vasc. Biol, 2002, vol. 22, pp. 1058-1061.*
Juppner, Bone, 1995, vol. 17, No. 2, pp. 39S-42S.*

* cited by examiner

*Primary Examiner* — Sarae L Bausch
(74) *Attorney, Agent, or Firm* — Bond Schoeneck and King PLLC; David Nocilly

(57) ABSTRACT

An assay for a GCH1 allele and associated genotype for the screening, prediction, diagnosis, prognosis, treatment and treatment response of psychiatric, neuropsychiatric, and neurological disorders, such as schizophrenia, schizoaffective disorder and bipolar disorder, and for defining treatments of such disorders. The presence of a variant in the GCH1 gene, alone or in conjunction with a measurement of low or altered biopterin, or altered BH4 system measures, is used to screen or diagnose subjects at risk for developing a psychiatric, neuropsychiatric, or neurological disorder. The genetic assay, with or without a biopterin or BH4 system assay, may also be used to determine treatment regimens. For subjects with an impaired BH4 system, treatments to increase or normalize biopterin, BH4, or the BH4 system can also be used, such as BH4 supplementation, lithium treatment, phenylalanine treatment, or other treatments and therapies.

2 Claims, 8 Drawing Sheets
Specification includes a Sequence Listing.

```
       TCAAG TGAGGAAAAA GGTCCATTTA TTAATCTCAA AGAAAACAGT
TACAGCAGAT GTCACTGGTT AAGAGTTCAG TTGGTGAATA GCATTTCACA
ATTTGTACCA ACATCTGGGG AAAGACGCTT TGCATGGAAC TGTAAAACAA
TTGAGCACCA AATCTGCACA ACTGCGTTTC TAGAAAATGC GATGGGTTTT
ATAGAGATGA GGTCTTGCTA TGTTTTCCAG GCTGGTCTCG AACTCTTGGC
CTCAAGCGAT CCTCCCGCCT CGGTCTCCCC AAGCGCCGGG AGTACAGGCG
TGAGCCACCG ACGGAAATGG ATTTTAAGTG AAAGTCCTAT CTTCGTTTGC
AAATCA

TCAAG TGAGGAAAAA GGTCCATTTA TTAATCTCAA AGAAAACAGT
TACAGCAGAT GTCACTGGTT AAGAGTTCAG TTGGTGAATA GCATTTCACA
ATTTGTACCA ACATCTGGGG AAAGACGCTT TGCATGGAAC TGTAAAACAA
TTGAGCACCA AATCTGCACA ACTGCGTTTC TAGAAAATGC AATGGGTTTT
ATAGAGATGA GGTCTTGCTA TGTTTTCCAG GCTGGTCTCG AACTCTTGGC
CTCAAGCGAT CCTCCCGCCT CGGTCTCCCC AAGCGCCGGG AGTACAGGCG
TGAGCCACCG ACGGAAATGG ATTTTAAGTG AAAGTCCTAT CTTCGTTTGC
AAATCA

GCH1 Forward Primer:    TCAAGTGAGGAAAAAGGTCCA
GCH1 Reverse Primer:    TGATTTGCAAACGAAGATAGGA
```

FIG. 5

SYSTEM AND METHOD FOR DIAGNOSIS AND TREATMENT OF NEUROPSYCHIATRIC DISORDERS

CROSS-REFERENCE TO RELATED APPLICATIONS

The present application is a continuation of U.S. patent application Ser. No. 14/069,847, filed on Nov. 1, 2013, which was a continuation of U.S. patent application Ser. No. 13/323,413, filed on Dec. 12, 2011, which was a continuation of U.S. patent application Ser. No. 11/873,971, filed on Oct. 17, 2007, now U.S. Pat. No. 8,076,075, which claimed priority to U.S. Provisional Application Ser. No. 60/829,856, filed Oct. 17, 2006.

STATEMENT REGARDING FEDERALLY SPONSORED RESEARCH

This invention was made with government support under Grant Nos. MH067941 and MH066883 of the National Institutes of Health (NIR). The government has certain rights in the invention.

BACKGROUND OF THE INVENTION

1. Field of the Invention

The present invention relates to psychiatric and neuropsychiatric disorders, such as schizophrenia, schizoaffective disorder, bipolar disorder, and Alzheimer's disease and, more particularly, to the role of GTP cyclohydrolase I gene, GTP cyclohydrolase (GTPCH), biopterins, and tetrahydrobiopterin in the detection, diagnosis, prognosis and treatment of such disorders.

2. Description of the Related Art

Schizophrenia (SZ) and schizoaffective disorder (SaD) are among the most common forms of mental illness, and have large genetic and heritable components, indicated by studies showing increased risk among first degree relatives, and concordance between mono- and dizygotic twins. The genetic components of SZ and SaD appear to involve multiple genes. Individuals with these psychiatric disorders can display an overlapping range of symptoms and there appears to be increased prevalence of SZ in the families of SaD sufferers, and vice versa. There have also been reports of shared genetic susceptibility loci for these disorders.

Tetrahydrobiopterin (BH4) is a vital cofactor maintaining availability of the amine neurotransmitters, dopamine (DA), noradrenaline (NA), and serotonin (5-HT). BH4 is also involved in regulating the synthesis of nitric oxide (NO) by nitric oxide synthases (NOS), and stimulating and modulating the glutamatergic system. In the central nervous system (CNS), BH4 has also been shown to stimulate the release of DA, 5-HT and glutamate, as well as regulating the expression of tyrosine hydroxylase at nerve terminals. Plasma total biopterins level (biopterin) is a measure of BH4 (approximately 80-90% in the form of BH4) and are correlated with CNS biopterin levels.

Conventional methods do not rely on a genetically based method for assessing the presence or risk of schizophrenia or schizoaffective disorder using the GTP cyclohydrolase I (GCH1) gene alone or in conjunction with a biochemical assay. These methods also fail to disclose a method of treating psychiatric and neuropsychiatric diseases, such as schizophrenia, by addressing genetic deficiencies in the GCH1 gene and/or in the BH4 system. For example, there is currently no useful genetic test for determining subjects that are at-risk for developing schizophrenia and, as a result, treatment approaches have limited success.

BRIEF SUMMARY OF THE INVENTION

It is therefore a principal object and advantage of the present invention to provide a system and method for assessing the presence or risk or severity or progression or prognosis of certain psychiatric and neuropsychiatric diseases, and neurological disorders.

It is an additional object and advantage of the present invention to provide a system and method for testing for the presence or risk of psychiatric, neuropsychiatric, and neurological disorders.

It is a further object and advantage of the present invention to provide a system and method for the determination of treatment of psychiatric and neuropsychiatric diseases, and neurological disorders.

It is a further object and advantage of the present invention to provide a treatment for psychiatric and neuropsychiatric diseases, and neurological disorders.

In accordance with the foregoing objects and advantages, the present invention provides for genetic testing of GCH1, either as a stand-alone test, or in conjunction with assay of biopterin, BH4, and/or BH4 system measures for the assessment of psychiatric and neuropsychiatric diseases, such as schizophrenia, either alone or in conjunction with assays of other genes. Symptom scales, behavioral measures, physiological testing, biological or molecular or genetic testing, and imaging analyses, will also be used where appropriate, in conjunction with genetic testing, assay of biopterin, BH4, or BH4 system measures. In particular, a GTP cyclohydrolase I (GCH1) gene variant (nucleotide variant −959 nt G/A: rs10137071, NCBI dbSNP database) "A" allele, is present in a much larger than expected proportion of psychiatric patients (schizophrenics (SZ) and schizoaffective disorder (SaD)), than in healthy people. For example, the odds ratio of having the GCH1 variant genotype was over five fold higher in SZ and SaD patients when compared to healthy control subjects. The risk of having a psychiatric disorder is therefore multiplied by five times for people who carry the "A/A" variant.

The present invention is based on an assay of GCH1 genotype, separately and/or in conjunction with assay of biopterin or other pterins in blood, plasma, serum, CSF, or other fluids or tissues, and/or assays of other BH4 system measures, and is useful in the prediction, diagnosis and prognosis of psychiatric disorders, and for defining treatments. In addition, treatments such as BH4, biopterin, other pterin species, phenylalanine, lithium, or other treatments designed or known to increase biopterin or BH4 (or normalize the BH4 system) in persons with a variant GCH1 genotype (and thus to alleviate biopterin deficit or to prevent a deficit in persons at-risk for the disorders), may be administered to provide a therapeutic or preventative response or treatment in patients with the disorders or at-risk for developing the disorders. The assay of GCH1 genotype, with or without biopterin or BH4 assay, may also be used to determine antipsychotic or mood stabilizer medication, as well as other treatment requirements. For subjects with an impaired BH4 system, treatments to increase BH4 or normalize BH4 can be used, such as supplementation with BH4

(or other pterin molecule species), lithium treatment, phenylalanine treatment, or other useful treatments, such as ECT.

BRIEF DESCRIPTION OF THE DRAWINGS

The present invention will be more fully understood and appreciated by reading the following Detailed Description in conjunction with the accompanying drawings, in which:

FIG. 5 illustrates the sequence of the "g" allele of the GCH1 variant of the present invention (SEQ ID NO:1), the sequence of the "a" allele of the GCH1 variant of the present invention (SEQ ID NO:2), the sequence of the forward primer according to the present invention (SEQ ID NO:3), the sequence of the reverse primer according to the present invention (SEQ ID NO:4).

DETAILED DESCRIPTION OF THE INVENTION

Figure 1A:
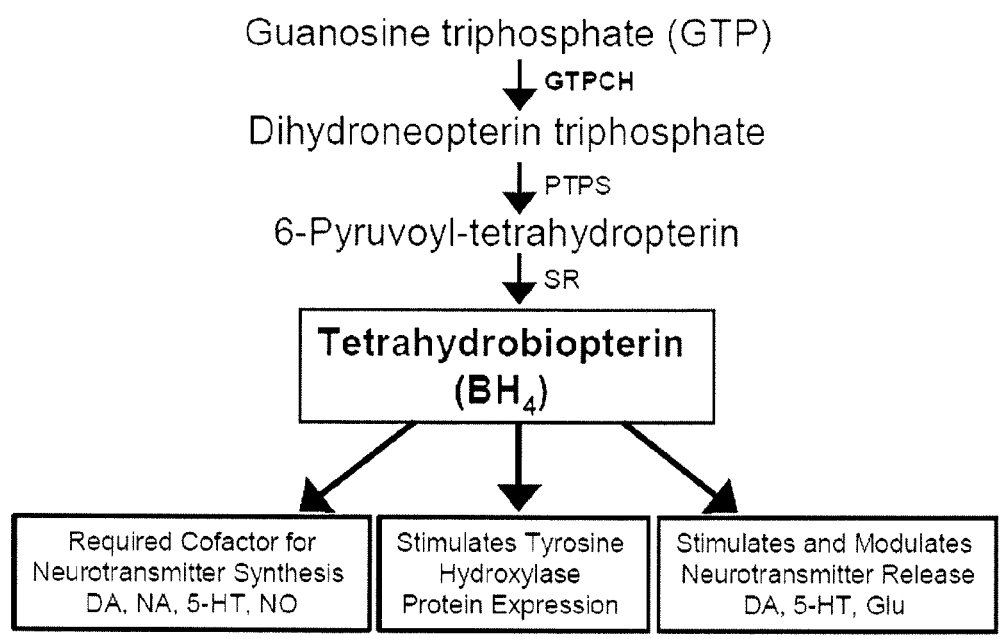
FIGS. 1A and B are schematics of biosynthesis pathways of BH4 and its roles in the hydroxylation of the aromatic amino acids to the amine neurotransmitters, nitric oxide (also as a cofactor) and its roles in stimulation and modulation of neurotransmitter synthesis and release.
Figure 1B:
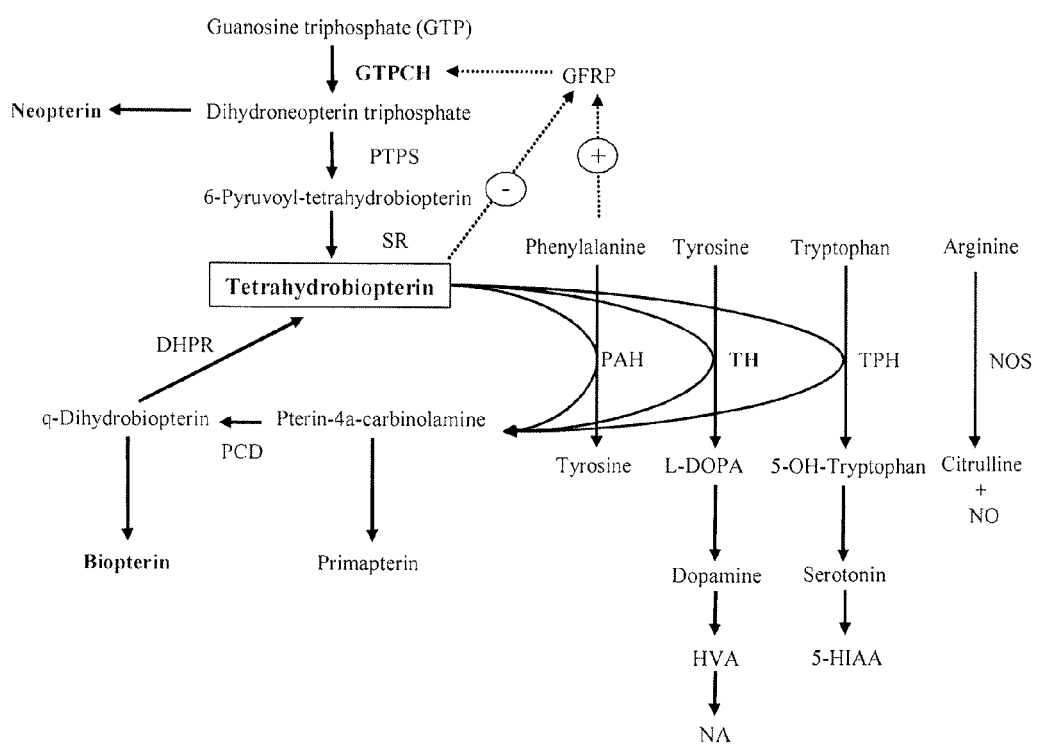

The present invention provides a screening (including population screening), risk assessment, prognostic and diagnostic test for SZ and SaD, and, if genetic and biochemical testing is combined, a screening, risk assessment, diagnostic and prognostic test for bipolar disorder (BpD). In addition, the present invention provides for treatments such as biopterin, BH4 or other pterin species (which have been successfully used to treat autism and other disorders in children, and depression and other disorders in adults, and so safe therapeutic doses have previously been determined), other treatments that increase BH4 (such as lithium) or biopterin, treatments which alleviate the biopterin deficit or the potential biopterin deficit in those at risk, or treatments which may be used to normalize BH4. The present invention is therefore be used to allow determinations of treatment use, and to provide treatments for alleviating psychiatric, neuropsychiatric, or neurological symptoms. The present invention will also provide for early detection and prophylactic or preventative treatment for those at risk for developing the disorders, such as children and adolescents, or others at risk.

The present invention further allows for assessment of GCH1 genotype alone, or in conjunction with assessment of one or more of biopterin, BH4, neopterin or other pterins, GCH1 RNA, epigenetic modifications including DNA methylation, GTPCH protein levels, GTPCH enzyme activity and/or the BH4 system, that can be used to determine treatment needs. The present invention may also be used to diagnose and/or prognose and/or determine treatment, for other disorders including but not limited to those described herein.

The term "BH4 system" includes biopterin (total biopterins or individual biopterin species), BH4, neopterin (total neopterins or individual neopterin, such as dihydroneopterin trophosphate), other pterin species, and/or the genes, RNA, proteins, and enzymes that form the pathways of BH4 biosynthesis and metabolism (including the de novo synthesis, regeneration, and salvage pathways, and cofactor reaction pathways). The term also includes genes, RNA, proteins, enzymes and metabolites that can directly and/or indirectly influence the biosynthesis of BH4 and/or the pathways of BH4 biosynthesis and metabolism, including the de novo synthesis, regeneration, and salvage pathways, and cofactor reaction pathways and associated genes, including the genes GCH1 GCHFR, PTS, SPR, PCBD, QDPR, NOS(I,II,III), PAH, TH, TPH, DHFR, MTHFR, AKR1B1, AKR1C3, AKR1C1, CBR1, NR4A2, CTF1, IL6, MTPN,LIF, CNTF, PRKG2, and the genes, proteins, enzymes, and/or metabolites relating to GSK3 alpha and/or beta, NURR1 and/or Nur77, Nurr1 and/or NOR1, IMPase and/or inositol phosphate-1-phosphotase (IPP), v-akt murine thymoma viral oncogene homolog 1 (AKT1), AKT/PKB, AKT2, AKT3, etc. The term BH4 system also includes the promoters, enhancers, supressors, and other regulatory regions, regulatory RNAs (such as microRNA) of "BH4 system" genes. The term BH4 system also includes epigenetic regulation such as methylation of BH4 system genes, and acetylation and/or ubiquitylation of chromosome-associated proteins such as histones.

The term "assay of BH4 system measures" includes assays and/or measurements of biopterin or BH4 or BH4 system DNA, RNA, genes, miRNA, methylation, acetylation, ubiquitylation, proteins, enzymes, and/or metabolites, other pterin species, GCH1 RNA, GTPCH protein, and/or GTPCH enzyme activity (and the RNA, protein and enzyme activities of the other BH4 system genes, including GCH1 GCHFR, PTS, SPR, PCBD, QDPR, NOS(I,II,III), PAH, TH, TPH, DHFR, MTHFR, AKR1B1, AKR1C3, AKR1C1, CBR1, NR4A2, CTF1, MTPN,LIF, CNTF, PRKG2), whether in plasma, serum, blood, CSF, urine, or saliva, as well as other tissues, fluids, cells, organs or substances. Assays of BH4 system measures, e.g., assays of biopterins, BH4, neopterins, and pterin species, include the use of HPLC methods. Assay of BH4 system measures also includes use of mass spectrometry methods, immunoassay, radioimmunoassay, immunohistochemistry, MRS, spectroscopy methods, radio-tracer assay and/or imaging methods, electrophoresis methods, molecular biology methods, including PCR and real time PCR, genetic sequencing methods, SNP assay methods, biochemical measurement methods, enzyme activity measurement methods, protein measurement methods, DNA, RNA, miRNA or protein microarray assay methods, other DNA, RNA and protein multiplex assay methods, and other assay and measurement methods known to those skilled in the art.

The term "psychiatric disorders" includes but is not limited to: SZ, SaD, BpD, mood disorders and personality disorders, unipolar depressive disorder, psychotic disorders, major depressive and other depressive disorders, other affective disorders, attention deficit disorder, delusional disorder, anxiety disorders, obsessive compulsive disorder, paranoid schizotypal or schizoid personality.

The term "neuropsychiatric disorders" includes, but is not limited to, neurological, neuropsychiatric and neurodegenerative disorders, including Alzheimer's disease, Pick's disease, Parkinson's disease, Huntington's disease, multiple sclerosis, Wilson's disease, Creutzfeldt-Jakob disease and other disorders of the central nervous system and the peripheral nervous system including abnormal or heightened pain sensitivity, as well as movement disorders including dyskinesias, dystonias and akathisias, autism, Asperger's syndrome and spectrum disorders, and autism spectrum disorders, and also dementias, cognitive status and decline, intellectual status and decline, learning or memory status decline, and other intellectual disabilities and disorders.

The term "patient" includes human subjects, including fetuses, as well as includes organ, tissue, cell, fluid, DNA, RNA, protein, chemical and/or material samples from patients and other organisms (e.g., animals). The term model includes animal models of diseases and states, and chimeric models.

The term "assay of GCH1 genotype" includes, but is not limited to, determination of the −959 nt G/A: rs10137071 GCH1 genotype and/or one or more other genetic change affecting GCH1, as well as genetic or epigenetic difference such as a nucleotide variant affecting the GCH1 gene or a copy number polymorphism or duplication, deletion or other mutation or change, in GCH1 or its promoters, enhancers, suppressors and other regulatory regions, and any other RNA species, e.g., regulatory RNAs such as miRNAs that regulate GCH1 gene expression. The term "assay of GCH1 genotype" also includes determination of epigenetic regulation such as DNA methylation, and/or acetylation and/or ubiquitylation of chromosome-associated proteins such as histones, affecting the GCH1 gene.

The term "normalize their BH4 system levels" includes treatment to normalize biopterin(s), other pterin species levels, BH4 levels, GCH1 RNA, GTPCH protein, tyrosine hydroxylase, tryptophan hydroxylase levels, the activities of the BH4 system enzymes, and/or the function of the BH4 system. The term "normalize their BH4 system levels" also includes treatment to normalize or treat or alter or supplement, the sequences and/or function of BH4 system genes and/or their regulatory regions or epigenetic regulators, including by gene therapy methods. For example, treatment may occur by introduction of nucleic acids to provide adequate and/or functional and/or normal gene functioning, to those in need of treatment, including those with, or at risk of developing a psychiatric or neuropsychiatric or neurological disorder. One or more nucleic acids can be provided or introduced to patient's bodies, cells, organs, tissues or fluids. Nucleic acids to be provided can include for example one, or more than one different, or several different, GCH1 nucleic acids, such as an oligonucleotide incorporating the gene variant (nucleotide variant −959 nt G/A: rs10137071, NCBI dbSNP database) "G" nucleotide, using methods known to those skilled in the art.

The term "a GCH1 variant" includes the −959 nt guanine/adenine (G/A): rs10137071 GCH1, "A" allele and/or "G/A" or "A/A" genotype and/or other genetic change(s) affecting GCH1.

The term "useful treatments" includes treatment with pterin(s) and/or other molecules, including BH4, biopterin, dihydrobiopterin, sepiapterin, sapropterin, dihydroneopterin triphosphate or other neopterins, Lithium (Li) or Li-based medications, phenylalanine, aspartame, sapropterin dihydrochloride, peptide molecules containing residues such as phenylalanine, tyrosine, and/or tryptophan, inhibitors of glycogen synthase kinase 3 (beta and/or alpha) expression, enzyme activity, or catalysis, inositol phosphate-1-phosphotase (IPP) expression, enzyme activity, or catalysis, Inositiol monophosphate (IMPase) expression, enzyme activity, or catalysis, promoters or inhibitors of AKT expression, enzyme activity, or catalysis, promoters of glycogen synthase kinase 3 (beta and/or alpha) phosphorylation, administration of electrical stimulation and/or electroconvulsive therapy (ECT), transcranial magnetic stimulation (TMS), electrical brain stimulation, deep brain stimulation and/or other electrical, magnetic or radiowave general or focally targeted brain stimulation, and/or inositol depletion treatments. Useful treatments may also include neuroleptic(s) and/or other antipsychotic and/or mood stabilizer(s) and/or other psychotropic(s) and/or other medication(s)

The term "low biopterin" includes, but is not limited to, biopterin levels (or other BH4 system measures) that are either lower than the mean, median, mode, "normal" level, or reference range level for control or healthy subject groups (groups can be defined by factors including but not limited to, ethnicity, race, age, gender, BMI, weight, nutritional status, health status). The term "low biopterin" also includes levels that are outside of levels needed for optimal or normal brain, CNS, biological, biochemical, and/or physiological function. Subject biopterin level can also be adjusted to reflect the influence of modifiers of biopterin level, BH4 level, and/or Phe levels, such as that due to nicotine, or to treatments such as lithium, ECT, TMS, deep brain stimulation, or other treatments or therapies. Low biopterin can also be defined as a range or level compared to different population(s) and/or group norms and/or arbitrary cutoffs. Abnormal biopterin levels can also include elevated or "high" BH4 system measures.

The definitions, such as those described above, can also be utilized to define "low" biopterin, BH4 or other measures, such as other pterin species, GCH1 RNA, GTPCH protein, and/or GTPCH enzyme activity, or other BH4 system measures. Definitions can also be based upon comparisons (e.g., with reference ranges) and/or statistical descriptions including those such as percentiles, standard deviations, confidence intervals, standard errors, etc.

The present invention is based on the fact that a GTP cyclohydrolase I (GCH1) homozygous gene variant (nucleotide variant −959 nt G/A: rs10137071, NCBI db SNP database) "A" allele, is present in a much larger than expected proportion of psychiatric patients (schizophrenics (SZ) and schizoaffective disorder (SaD)), than in healthy people. For example, the odds ratio of having the GCH1 variant genotype was nearly five fold higher in SZ and SaD patients when compared to healthy control subjects. The risk of having a psychiatric disorder is therefore multiplied by five times for people who carry the "A/A" variant.

Patients with the GCH1 "A" allele and, in particular, the "A/A" genotype, have decreased fasting blood plasma levels of a total biopterins, known as "biopterin," that is from, and is a measure of tetrahydrobiopterin (BH4). BH4 is a vital cofactor that is required for the maintenance of neurotransmitters in the brain and periphery, and these neurotransmitters have been implicated in psychiatric disorders. The GTP cyclohydrolase I (GCH1) gene encodes GTP-cyclohydrolase (GTPCH), the first enzyme in BH4 biosynthesis. This finding directly links the GCH1 gene "A" variant to the increased risk for these psychiatric disorders.

As the GCH1 "A" variant is a risk allele for SZ, SaD, and BpD, having the GCH1 variant genotype has biological consequences that likely results in decreased GCH1 gene expression or altered GCH1 splicing, and thus the decreased biopterin level observed in patients with the variant "A" allele. As GCH1 encodes an enzyme that is required for BH4 biosynthesis (called GTPCH), lower or altered GCH1 expression likely results in the plasma biopterin deficit in SZ and SaD populations. SZ patients have lower GCH1 gene expression than healthy control subjects, and SZ subjects with the GCH1 "A" allele have lower GCH1 expression than SZ without the "A" allele, and thus are likely to exhibit a similar brain biopterin deficit (or BH4 system deficit) that will result in the dysregulation of neurotransmitters, such as dopamine, noradrenaline, serotonin and the glutamatergic system, nitric oxide, and with result in an SZ, SaD, or other psychiatric or neuropsychiatric disorder or neurological disorder phenotype. Similarly, GCH1 expression is lower in "A" allele BpD patients compared to BpD without the A allele, and these BpD patients are also likely to exhibit a similar brain biopterin deficit (or BH4 system deficit) that will result in the dysregulation of neurotransmitters, such as dopamine, noradrenaline, serotonin and the glutamatergic system, and nitric oxide.

BpD patients treated with Li, have higher levels mRNA levels of GCH1, compared to patients not treated with Li. Also, BpD subjects treated with Li and who have the GCH1 "A" allele had lower GCH1 expression than BpD subjects who were also treated with Li, but did not have the "A" allele. It is likely that Li upregulation of GCH1 is modulated by the GCH1 gene sequence, and Li treatment may be less effective, or have different efficacy, in patients with the GCH1 "A" allele.

The present invention therefore involves the assay of GCH1 genotype, separately and/or in conjunction with assay of biopterin, BH4, other pterins in plasma, other BH4 system measures, CSF, serum, urine, or other cells, tissues, organs, and fluid, and is useful in the screening, prediction, diagnosis and prognosis of psychiatric disorders, and for defining treatments. In addition, treatments such as BH4, biopterin, other pterin species, Phe, lithium, or other treatments designed or known or considered to increase biopterin or BH4 in persons with a variant GCH1 genotype (and thus to alleviate biopterin or BH4 system deficit, or prevent manifestation of a biopterin deficit in those at risk), will be administered to provide a therapeutic or preventative response or treatment in patients with the disorders or at-risk for developing the disorders. The present invention will be useful for determination of risk, screening, early detection, diagnosis, and treating psychiatric disorders including SZ, SaD, bipolar disorder (BpD), mood disorders and personality disorders, unipolar depressive disorder, psychotic disorders, major depressive and other depressive disorders, other affective disorders, attention deficit disorder, delusional disorder, anxiety disorders, obsessive compulsive disorder, paranoid schizotypal or schizoid personality.

Patients with Alzheimer's disease (AD) also have decreased biopterin and/or BH4 levels. The present invention may thus be useful for determination of risk, screening, early detection, diagnosis, and treating AD and other neurological and neuropsychiatric and neurodegenerative disorders, including Pick's disease, Parkinson's disease, Huntington's disease, multiple sclerosis, Wilson's disease, Creutzfeldt-Jakob disease and other disorders of the central nervous system and the peripheral nervous system, and movement disorders including dyskinesias, dystonias and akathisias, and dementias, as well as in intellectual or cognitive status impairment or decline. The same diagnostic and/or prognostic and/or treatment approaches would apply for these disorders, as with psychiatric disorders such as those outlined below for SZ and/or SaD and/or BpD.

The present invention also encompasses the screening, detection, prediction, diagnosis, early detection, prognosis, and/or treatment of disorders where a genetic or epigenetic (e.g., methylation and/or acetylation and/or ubiquitylation) difference affecting the GCH1 gene and/or its promoters, enhancers, suppressors and other regulatory regions and/or RNA species (e.g., regulatory RNAs, such as miRNAs or non-coding RNA), is present, such as a nucleotide variant, deletion, duplication, mutation, or change. The present invention further includes the generation of genetic therapy treatments designed to provide GCH1 DNA, RNA and/or GTPCH protein to subjects in need of treatment, and that do or do not carry deleterious variants. The present invention further includes the generation of genetic therapy treatments designed to provide BH4 system DNA, RNA, and/or protein(s) to subjects in need of treatment. Subjects determined to be at-risk for development of a psychiatric, neuropsychiatric or neurological disorder, can include infants, children, adults, gametes, embryos, and/or fetuses, and assessment of risk status can be made from the individual, parental, and/or prenatal testing.

The present invention also encompasses kits for the screening, detection, prediction, diagnosis, early detection, prognosis, and/or treatment of disorders where a genetic or epigenetic (e.g., methylation and/or acetylation and/or ubiquitylation) difference affecting the GCH1 gene and/or its promoters, enhancers, suppressors and other regulatory regions and/or RNA species (e.g., regulatory RNAs, such as miRNAs or non-coding RNA), is present, such as a nucleotide variant, deletion, duplication, mutation, or change. As described herein, the present invention includes primers that may be used to identify the presence of the GCH1 alleles in humans.

Assessment of risk or screening is performed by genotyping subjects, along with, or without, a biopterin, BH4, BH4 system, other pterin system measurement (e.g., fasting plasma biopterin, GCH1 RNA, GTPCH protein and/or neopterin measurement. Subjects with the rs10137071 GCH1 "A/A" variant genotype alone or in conjunction with a "low" or "altered" BH4 system measure (e.g., biopterin), or the "A/G" or "A/A" genotype (or other DNA variants of the GCH1 gene) in conjunction with a measurement of "low" or "altered" biopterin (BH4, marker of low BH4, GCH1 RNA, and/or GTPCH protein), and/or other BH4 system measures, would be considered at an increased risk for developing a psychiatric disorder.

In addition, subjects with the variant genotype, low or altered biopterin, BH4, or BH4 system, altered GCH1 RNA, and/or GTPCH protein levels would be medicated with one or more of biopterin or BH4 or other pterin species, or Phe or other treatment that increases BH4 (such as lithium) or inositol depletion, to alleviate the deficit, or treatment to increase or supplement BH4 or biopterins, such as electrical brain stimulation or electroconvulsive therapy (ECT) or transcranial magnetic stimulation (TMS).

Assessment of biopterin and/or BH4 and/or other pterin levels, along with GCH1 genotyping will also be used for screening or assessing those at-risk for developing a psychiatric, neuropsychiatric, or neurological disorder, allowing for heightened monitoring, early detection, and early, prodromal or prophylactic initiation of treatments. For those at-risk or with the disorders, treatment decisions can be made based on genotyping and/or biopterin or BH4 level assay, and/or GCH1 RNA, GTPCH protein level(s), and/or BH4 system measures.

The assay of GCH1 genotype, with or without biopterin or BH4 assay, can be used to determine antipsychotic and/or mood stabilizer medication, and/or other treatment requirements. The efficacy of different medications and/or dosages will vary with genotype and biopterin and/or BH4 and/or GCH1 RNA and/or GTPCH protein level(s). For subjects with an impaired BH4 system (indicated by low biopterin, for example), treatments to increase BH4 can be used, such as BH4 supplementation, lithium treatment (patients treated with lithium have increased biopterin levels), phenylalanine treatment, or other treatments, such as ECT, TMS, etc.

FIGS. 1A and B show the biosynthesis pathways of BH4 and its central role in the hydroxylation of the aromatic amino acids to the amine neurotransmitters, and its role as a cofactor in nitric oxide synthesis, and in the synthesis and release of neurotransmitters. In FIGS. 1A and B, GTPCH refers to GTP cyclohydrolase I, encoded by the GCH1 gene, PTPS refers to 6-pyruvoyl-tetrahydropterin synthase, encoded by the PTS gene, SR refers to sepiapterin reductase, encoded by the SPR gene, DA refers to dopamine, NA refers to noradrenaline, 5-HT refers to 5-Hydroxytryptamine, serotonin, NO refers to nitric oxide, and Glu refers to Glutamate.

As the amine neurotransmitter and glutamatergic systems and NO activity have been implicated in the etiology of schizophrenia and affective disorders, a study of fasting plasma total biopterin (a measure of BH4) was performed. Study subjects included patients with BpD (n=27), SZ (n=154), SaD (n=59), and control subjects (n=37). For each patient, a lifetime psychiatric diagnosis (using DSM-III-R criteria) was determined based on (a) clinical data collected from current and previous admissions, and (b) diagnostic interviews. For control subjects, an interview and internal scale were completed to determine the presence of personal and/or family history for psychiatric, neurological, and medical conditions. Demographics were collected for each of the subject groups, that included age, gender, ethnicity, years on neuroleptics (NL), and chlorpromazine equivalent dose (CPZE) (for the 21 days prior to blood draw), and the 4 groups (controls, BpD, SZ, SaD) were not significantly different for the variables of age, gender, ethnicity distribution and body mass index. There was a significant difference in CPZ equivalence among patient groups, but no correlation between CPZ equivalence (i.e., neuroleptic use) and biopterin levels was observed.

To test for differences in biopterin levels between the diagnostic groups an initial GLM was used, with total biopterin as the primary outcome variable. This model, with the study group, the covariates of gender, age, ethnicity, years of NL group, and CPZE group, 24 hour dietary Phe/protein ratio and plasma Phe, showed significant or near significant main effects, or trends (on primary outcome variable of fasting total biopterin), only for the variables of study group, ethnicity, and plasma Phe. A final model revealed only study group and plasma Phe as significant predictors of variation in total biopterin with ethnicity approaching significance. Analysis of the main effects revealed that study group explained more than four times the amount of variation in log biopterin (Partial Eta Squared=0.112) than the variance explained by log Phe (Partial Eta squared=0.024). Pairwise comparisons of log biopterin estimated marginal means (controlling for log Phe and ethnicity) revealed significantly lower biopterin in SaD patients ($p<0.001$) and SZ patients ($p<0.0001$) than controls; specifically a plasma biopterin deficit of 34 percent in SZ patients and of 25 percent in SaD patients, when compared to the healthy control subjects, after partialling out the effects of potential confounds including gender, age, ethnicity, neuroleptic use history and dose of current use, 24-hour dietary phenylalanine/protein ratio (relevant to BH4 synthesis) and plasma phenylalanine (Phe) which stimulates BH4 synthesis. Of interest, BpD patients had significantly higher biopterin than SZ patients (mean difference±standard error=0.200±0.071, $p<0.031$), and were not significantly different from controls. SaD patients showed no significant difference from SZ or BpD patients.

A previous study of urine biopterin excretion showed no elevation in SZ subjects when compared to controls, suggesting that the plasma biopterin deficit results from a BH4 synthesis defect rather than increased urine excretion.

Figure 2:
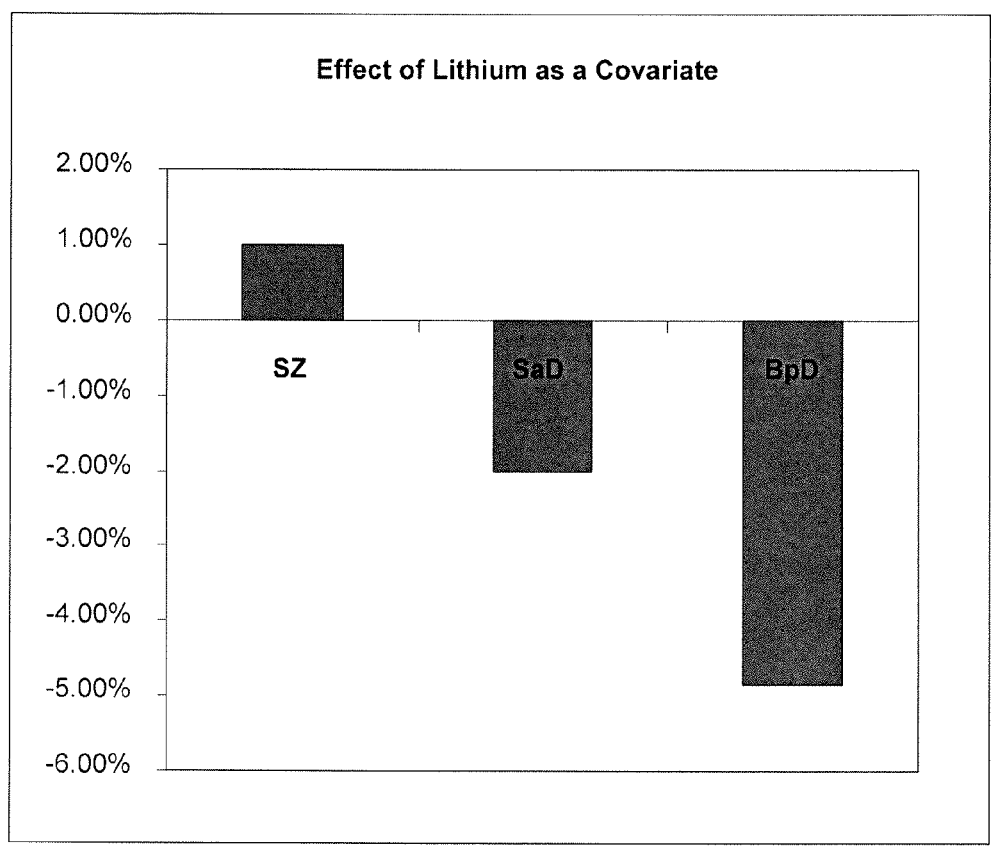
FIG. 2 is a chart illustrating the change in biopterin levels with lithium as a covariate.

In a further effort to explore the differences in plasma biopterin deficits between the psychiatric patient groups a second analysis was performed employing Lithium (Li) and mood stabilizer use as covariates on the model of plasma biopterin. In this new model, Li was found to have a significant main effect on plasma biopterin. Post-hoc analysis adjusted for multiple testing showed that, in this model, all patient groups had plasma biopterin levels significantly lower than control subjects. FIG. 2 illustrates the change in biopterin levels with Li as a covariate. This data suggests that Li treatment increases plasma biopterin levels. The percent change in adjusted least squares means is shown for each patient group in FIG. 2 when lithium (yes/no) was added to the final model (Li, Phe and ethnicity as covariates, on biopterin as the outcome variable). Post-hoc Tukey test (adjusted) demonstrated that SZ ($p<0.0001$), SaD ($p<0.0001$), and BpD($p=0.0179$) differ from controls. No significant differences were found between patient groups. 89 percent of the BpD patients were treated with Li, approximately 50 percent of the SaD patients, and 2 percent of the SZ patients. The final model demonstrated a plasma biopterin deficit of 32 percent, 27 percent, and 21.5 percent for SZ, SaD and BpD subjects respectively, when compared to controls.

DNA variants in a BH4 biosynthesis pathway gene thus appear to have a central role in the etiology of SZ, via dysregulation of BH4 Synthesis, which would manifest as a biopterin deficit. The rate-limiting and initial step in the de novo BH4 synthesis pathway is catalyzed by the enzyme GTP cyclohydrolase I (GTPCH (EC 3.5.4.16)) encoded by the GCH1 gene, which maps to chromosome 14q22. The present invention thus considered the genotype data for a biallelic nucleotide variant (−959 nt G to A: rs10137071, NCBI db SNP database) in the GCH1 gene promoter sequence, previously described as having association with bipolar disorder. The −959 nt G/A variant lies in the 5' upstream promoter of GCH1, and has a reported heterozygosity of 0.46 (23). Testing for association of this common variant with SZ and SaD in a mixed US sample of 174 subjects (86 SZ subjects, 42 SaD subjects and 46 control subjects) and testing for an association of GCH1 with the biopterin deficit in subject groups demonstrate that a GCH1 gene variant increases risk of major psychiatric disorders, and is associated with low biopterin levels in psychiatric patients. The results support a genetic basis for BH4 deficiencies in psychiatric disorders.

For each patient subject, a lifetime psychiatric diagnosis (using DSM-III-R criteria) was determined based on (a) clinical data collected from current and previous admissions, and (b) diagnostic interviews conducted by the research team. For control subjects, a questionnaire was completed to determine the presence of personal and/or family history for psychiatric illness. Control subjects had no history of psychiatric disorders, although 1 control subject had previously experienced mild, age-related depression, but had not sought treatment. After complete description of the study to the subjects, written informed consent was obtained.

Genomic DNA was extracted from whole blood using standard methods (Gentra Systems, Inc). Primers were utilized to amplify a 351 bp genomic region spanning the G/A variant in a 35 cycle PCR reaction. The restriction enzyme BsrD1 recognizes and cleaves the A allele resulting in the formation of a 191/160 bp doublet. Digested products were visualized following electrophoreses. Subjects homozygous for the G allele were genotyped by the presence of a single 351 bp band, heterozygous subjects have two visible bands, the 351 bp G allele and the 191/160 bp A allele, while A/A subjects have only the 191/160 bp doublet.

Sample preparation and assay for plasma total biopterin has previously been reported and measurement of plasma Phe (assayed due to its known role in the regulation of BH4 synthesis) has also been reported. Tests for Hardy Weinberg equilibrium, ethnic distribution of study groups, and initial model of association between GCH1 genotypes (A/A, GIA, GIG) and diagnostic group (SZ, SaD, C) were performed using exact tests. Under a recessive model (testing the difference between the minor allele (A) homozygotes versus GIA heterozygotes and major allele (G) homozygotes), logistic regression was employed to test for association with psychiatric group status. Wald chi-squares and odds ratios (OR) with Wald 95% Confidence Intervals (Wald CI) were reported with and without ethnicity as a covariate.

Functional analyses of the GCH1 genotype using logistic regression and general linear models were conducted on a subset of subjects with plasma biopterin data available. For logistic models, dependent variables were psychiatric status and independent variables were GCH1 genotype, biopterin level and the interaction of GCH1 genotype with biopterin level. Ethnicity was used as a covariate in the initial model.

A general linear model was used to test the effect of GCH1 genotype, psychiatric disorder status and their interaction on biopterin level. As the plasma concentration of Phe in fasting subjects has a significant effect on plasma total biopterin levels, and Phe was employed as a covariate to measure the effect of GCH1 genotype on biopterin level. Post-hoc significance testing was reported using a Tukey-Kramer adjustment for multiple comparisons in all logistic and linear models. Statistical analyses were conducted using SAS 9.1.2 (FREQ, LOGISTIC and GLM Procedures, SAS Institute Inc, 2004) and exact tests for Hardy Weinberg equilibrium were calculated using R with the genetics library (R: A language and environment for statistical computing. R Foundation for Statistical Computing, Vienna, Austria, 2006, version 1.2.0, 2005).

Exact tests for Hardy-Weinberg equilibrium demonstrated equilibrium for the patient (n=128, p=0.1534), and control groups (n=46, p=0.1299). Ethnic distributions of SZ, SaD, and control samples were not significantly different (Fisher exact test, n=174, p=0.4234). Overall frequencies: Patient group—42.2% Caucasian, 39.8% African-American, 18.0% Hispanic; Control group—56.5% Caucasian, 30.4% African-American, 13.1% Hispanic. Subject group demographics are presented in Table 1 below. Exact counts (and %) of GCH1 genotypes are shown for each of the study and ethnic groups. The A/A genotype was significantly associated with both SZ and SaD. Significance was observed in the African-American group and a trend toward significance in the Hispanic group. After adjusting for ethnicity, the associations detected in the recessive model remained significant in all groups tested.

TABLE 1

Diagnostic and Ethnic Group Comparison of GCH1 Genotype.

| | GCH1 Genotype | | | Wald Chi-Square (p =) | |
| --- | --- | --- | --- | --- | --- |
| Subjects (n = 174) | A/A | G/A | G/G | Recessive Model | Model (adjusted) |
| SZ (n = 86) | 30 (34.9) | 34 (39.5) | 22 (25.6) | 0.0024 | 0.0057 |
| Controls (n = 46) | 4 (8.7) | 27 (58.7) | 15 (32.6) | | |
| SaD (n = 42) | 12 (29) | 21 (50) | 9 (21) | 0.0216 | 0.0288 |
| Controls (n = 46) | 4 (8.7) | 27 (58.7) | 15 (32.6) | | |
| Patients (n = 128) | 42 (32.8) | 55 (43) | 31 (24.2) | 0.0033 | 0.0066 |
| Controls (n = 46) | 4 (8.7) | 27 (58.7) | 15 (32.6) | | |
| African-American (n = 65) | | | | | |
| Patients (n = 51) | 25 (49) | 21 (41.2) | 5 (9.8) | 0.0312 | — |
| Controls (n = 14) | 2 (14.3) | 12 (85.7) | 0 (0) | | |
| Caucasian (n = 80) | | | | | |
| Patients (n = 54) | 7 (13) | 28 (51.8) | 19 (35.2) | n/s | — |
| Controls (n = 26) | 2 (7.7) | 12 (46.15) | 12 (46.15) | | |
| Hispanic (n = 29)* | | | | | |
| Patients (n = 23) | 10 (43.5) | 6 (26.1) | 7 (30.4) | 0.0676 | — |
| Controls (n = 6) | 0 (0) | 3 (50) | 3 (50) | | |

*In the Hispanic group (n = 29), a valid maximum likelihood estimate could not be calculated and a Fisher Exact Test was performed. n/s, not significant In an initial analysis, an association between GCH1 genotype (A/A, A/G and GIG) and SZ (Fisher exact test, p=0.0027), and SaD (Fisher exact test, p=0.05) was revealed. When patient groups were combined, a significant association remained (n=174, Fisher exact test, p=0.0038). Most notably, under a recessive model the inventors found a highly significant association between the A/A genotype and SZ (Wald chi-square=9.2, df=1, p=0.0024) and significant association with SaD (Wald chi-square=5.3, df=1, p=0.0216). When the patients were combined (patients n=128 and controls n=46), a highly significant association remained (Wald chi-square=8.6, df=1, p=0.0033). The odds ratios (OR) of having a SZ or SaD diagnosis amongst the homozygous A/A population were 5.6, and 4.2 respectively. Combining the patient groups yielded an OR of 5.1.

Although subject ethnicities were not different between patient and control groups, assuming a degree of stratification in the mixed US population of the study, the inventors added ethnicity as a covariate in the model. The resulting OR's adjusted for ethnicity were 5.0 (p=0.0057, 95% Wald CI: 1.601-15.886), for SZ and 4.1 for SaD (p=0.0288, 95% Wald CI: 1.157-14.389), 4.7 combined patient group (p=0.0066, 95% Wald CI: 1.54-14.48). Thus, the A/A genotype confers a highly significant increased risk of having a psychiatric disorder.

The association of the A/A genotype with psychiatric disorders differed among ethnic groups within the study sample (see Table 1). In patient and control subject groups, the highest prevalence of the A/A genotype was found in the African-American subjects (patients 49.0%, controls 14.3%). Further association testing performed within the specific ethnic groups illustrated a significant association of the A/A genotype with diagnostic group in the African-American subset of patients, which was a trend in the Hispanic subjects. The A/A genotype was 69% more frequent in patients than controls in the Caucasian group.

Figure 3:
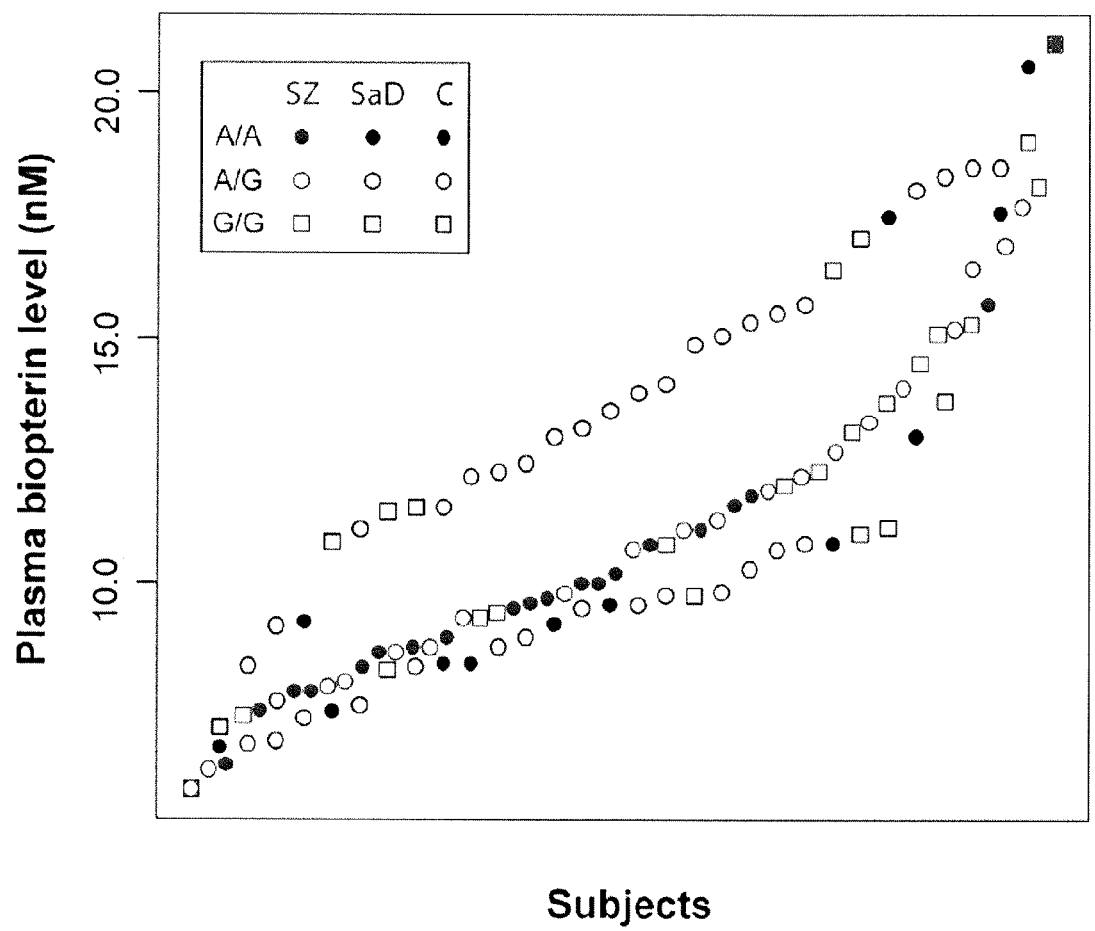
FIG. 3 is a graph of the ranked plasma biopterin levels and GCH1 genotype within test diagnostic groups.

The biological relevance of the GCH1 genotype was initially investigated through analysis of plasma biopterin and genotype interaction. The plasma biopterin level is significantly lower in SZ when compared to control subjects. There is seen in FIG. 3, an individual subject's ranked plasma biopterin levels and GCH1 genotype within each diagnostic group displayed by Study Group, Plasma Biopterin level and GCH1 Genotype. Subjects are ranked by biopterin level (increasing left-right) within their study group, illustrating both the decreased biopterin levels in the SZ (n=52) and SaD (n=32) subject groups compared to the control group (C, n=32), and the relative preponderance of A/A genotype among patients with the lowest biopterin levels. Plasma biopterin levels of the SZ and SaD subjects were not significantly different from each other, however both were significantly different from control subjects (p<0.01 for both SZ and SaD groups). BpD patients also had significantly lower biopterin than controls when biopterin levels were adjusted for the effects of Lithium treatment.

Table 2 below shows descriptive statistics for biopterin level (and standard deviations (SD)) for each subject group, separated by GCH1 genotype. Biopterin values and GCH1 Genotypes for subject groups (Patient and Control). The mean biopterin levels (nM) and standard deviation (SD) within each subject group is shown for each GCH1 genotype. Final biopterin values were adjusted by fasting Phe measurements.

TABLE 2

| Subjects | n | Mean Biopterin (nM) | SD | Adjusted Mean Biopterin (nM) |
| --- | --- | --- | --- | --- |
| Patients | 84 | | | |
| AA | 29 | 10.7 | 3.9 | 10.7 |
| AG | 35 | 10.8 | 3.4 | 10.8 |
| GG | 20 | 13.6 | 5.5 | 13.9 |
| A/A A/G | 64 | 10.7 | 3.6 | 10.8 |
| G | 20 | 13.6 | 5.5 | 13.9 |
| Controls | 32 | | | |
| AA | 3 | 17.5 | 6.5 | 17.2 |
| AG | 22 | 15.1 | 3.7 | 15.0 |
| GG | 7 | 15.1 | 5.2 | 14.7 |
| AA/AG | 25 | 15.4 | 4.0 | 15.2 |
| G | 7 | 15.1 | 5.2 | 14.7 |

Figure 4:
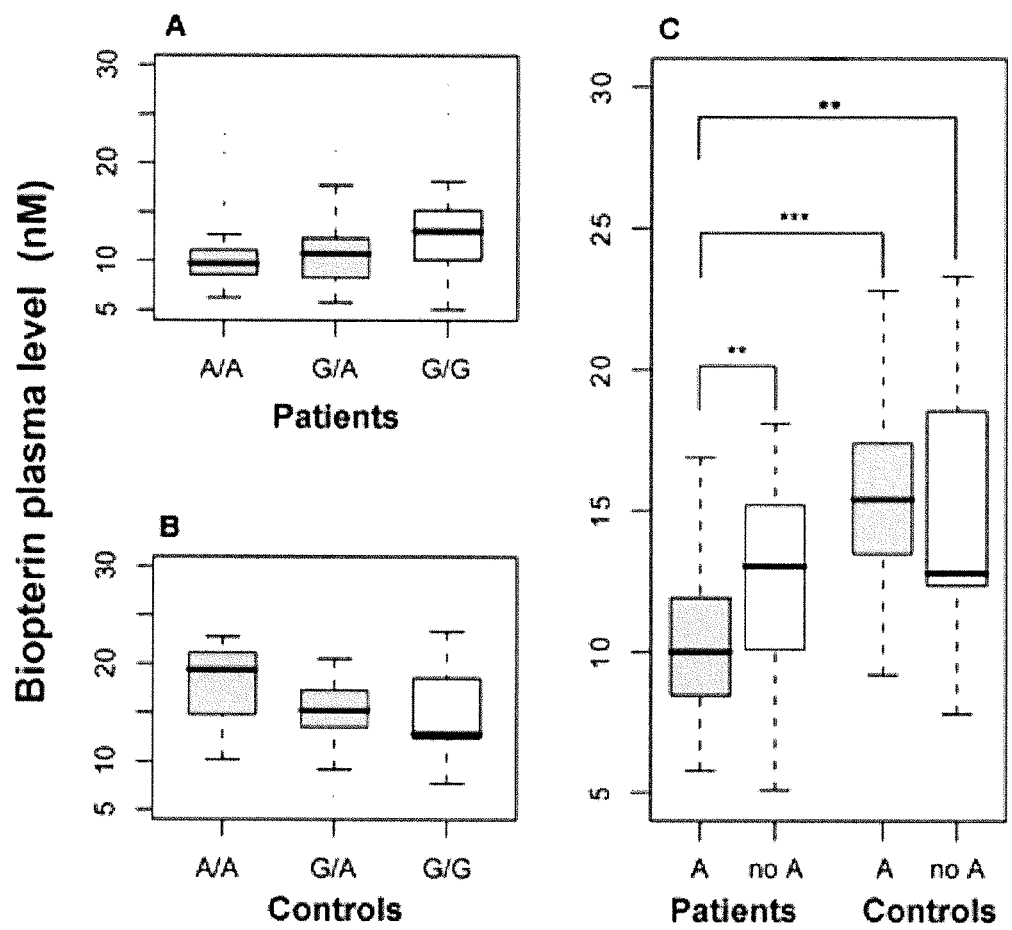
FIG. 4 is a graph of the plasma biopterin values and GCH1 genotypes for the test subject data.

The plasma biopterin values and GCH1 Genotypes for the subject group data is plotted in the FIG. 4 for patients (Panel A) and controls (Panel B). Plasma biopterin values (nM) (unadjusted for fasting phenylalanine levels) were plotted for patient subject genotype (Panel A), A/A (n=29), G/A (n=35) and G/G (n=20) and for control subject genotypes (Panel B), A/A (n=3), G/A (n=22) and G/G (n=7). No significant difference in biopterin level was observed between A/A or G/A genotypes in the patient group, however both the A/A and G/A patient groups were significantly different from the G/G patients (Tukey adjusted p-values for multiple comparisons: p=0.0165 and p=0.0168, respectively). Patient subject A allele carriers were combined for further analysis (patient A allele carriers-blue box-plots). No significant difference in biopterin level was observed among the control genotypes (control A allele carriers-pink box-plots). Panel C shows patient A allele carriers (n=64) have decreased biopterin levels compared to homozygous G/G patients (n=20), and to all control subject groups (lines indicate Tukey adjusted p-values for multiple comparisons: p<0.05, *p<0.0001). Box plots display the median (horizontal line in box), first (Q1) and third (Q3) quartiles (ends of the boxes). Bars outside the boxes represent the extreme values within 1.5 times the inter-quartile range (IQR) from the upper or lower quartile. Points at a greater distance from the median than 1.5 times the IQR are plotted individually as small circles.

A logistic regression analysis was performed using all subjects with both plasma biopterin level and GCH1 genotype (patient group n=84; control group n=32) and the interaction between plasma biopterin and GCH1 genotype was tested for the outcome variable "study group," controlling for ethnicity. Although the interaction between A/A genotype and biopterin on study group (Patient, Control) was not significant, and post-hoc comparisons did not show a significant difference between biopterin levels of patient subjects with the A/A and GIA genotypes, the mean biopterin levels of both A/A and GIA patient groups were significantly different to mean biopterin for GIG patients (A/A p=0.0165, A/G p=0.0168) and so the A/A and GIA patient groups were combined to form an A allele carrier group.

The interaction of GCH1 A allele and low biopterin level, was found to be a significant predictor of diagnostic group (patient or control) (Wald chi-square=4.8, df=1, p=0.0286). Ethnicity was not a significant predictor of study group (Wald chi-square=0.1, df=1, p=0.8962) and was thus removed from the final model (adjusted p-value of final model interaction, p=0.0276, model concordance at 79.8%). Table 3 below shows parameters from the logistic models. Logistic regression was employed to test the interaction between plasma biopterin level and GCH1 genotype, as a significant predictor of study group (patient or control, n=116), using ethnicity as a covariate in the initial model.

TABLE 3

GCH1 A allele Status and Biopterin Level as a Predictor of Study Group.

| Parameter | DF | Estimate | Standard Error | Wald Chi-Square | Pr > ChiSq |
| --- | --- | --- | --- | --- | --- |
| Initial Model[a] | | | | | |
| Intercept | 1 | 3.2294 | 0.8042 | 16.1268 | <.0001 |
| GCH1 A allele | 1 | 1.4525 | 0.8122 | 3.1982 | 0.0737 |

TABLE 3-continued

GCH1 A allele Status and Biopterin Level as a Predictor of Study Group.

| Parameter | DF | Estimate | Standard Error | Wald Chi-Square | Pr > ChiSq |
|---|---|---|---|---|---|
| Biopterin (n/M) | 1 | −0.1693 | 0.0535 | 10.0163 | 0.0016 |
| Biopterin * GCH1 A allele | 1 | −0.1179 | 0.0537 | 4.8213 | 0.0281 |
| Caucasian vs African American | 1 | −0.0178 | 0.3400 | 0.0028 | 0.9582 |
| Hispanic vs African American | 1 | 0.1531 | 0.4509 | 0.1153 | 0.7342 |
| Final Model[b] | | | | | |
| Intercept | 1 | 3.2055 | 0.7970 | 16.1774 | <.0001 |
| GCH1 A allele | 1 | 1.4206 | 0.7970 | 3.1772 | 0.0747 |
| Biopterin (n/M) | 1 | −0.1693 | 0.0536 | 9.9888 | 0.0016 |
| Biopterin * GCH1 A allele | 1 | −0.1180 | 0.0536 | 4.8531 | 0.0276 |

[a]Overall model: Likelihood Ratio chi-square = 22.9, df = 5, p = 0.0004, 80.1% Concordance rate
[b]Overall model: Likelihood Ratio chi-square = 22.7, df = 3, p < .0001, 79.8% Concordance rate Further supporting this detected interaction, tests showed that GCH1 allele status is itself a significant predictor of biopterin level. As fasting phenylalanine (Phe) levels are known to be predictors of plasma biopterin levels, adjustments were made for Phe. While the GCH1 allele did not have a significant main effect on plasma biopterin, levels within the patient group were significantly lower in patients with the A allele compared to those without (Tukey adjusted p-values for multiple comparisons, p=0.0208). In control subjects no significant difference in biopterin levels for GCH1 allele status was detected (Tukey adjusted p=0.9924) (see FIG. 3, which shows for unadjusted biopterin levels and significance testing between subject groups).

The sequence of the GCH1 promoter in which the GCH1 variant of the present invention lies is seen in FIG. 5. Also seen in FIG. 5 are the sequences for the forward and reverse primers that may be used to identify the GCH1 alleles of the present invention. The nucleotide sequence of the 351 bp DNA product that is amplified using the primer pair (green) is shown. The published SNP rs10137071 (the SNP rs10137071 is published as a CIT variant as the GCH1 gene is transcribed in the reverse DNA strand), also referred to as the −959 nt GIA variant, is underlined in the sequence (red) and the two possible alleles of the present invention are shown. Human subjects can be GIG, A/G or A/A at the relevant nucleotide position.

GCH1 mRNA transcripts are lower in peripheral tissues from A allele patient carriers. Whole blood leukocytes collected from subjects with SZ (both medicated and non-medicated SZ subjects), and BpD, and also ethnicity and gender matched control subjects, and global leukocyte gene expression were measured using Affymetrix microarrays. For each subject recruited, a 15 ml blood sample was collected. Immediately after blood collection, leukocytes were isolated by lysis of red cells, centrifugation and washing (Qiagen). Purified leukocytes were stored at −70° C. prior to RNA extraction (and are stable for periods of >1 year). Total RNA was extracted using RNeasy columns (Qiagen), and quantified by UV spectrometry using RNA standards for normalization or using an Agilent Bioanalyzer. Subjects were also genotyped for the GCH1 promoter variant, as described herein.

Only RNA samples with good quality ribosomal RNA, and satisfactory O.D. 260/280 ratios were processed to completion. 8 μg of total RNA was employed as a cDNA synthesis template, using an oligo-dT primer and Reverse Transcriptase (RT) enzyme, according to standard Affymetrix protocols. Purified cDNA, was then used as a template to generate biotin labeled cRNA (Enzo). cRNA samples were quantified and stored at −70° C. prior to fragmentation. 20 ng of each fragmented cRNA product was hybridized to an Affymetrix TEST3 array to check sample quality and then hybridized to an HU133 plus 2.0 array (containing over 40,000 transcripts).

Figure 6:
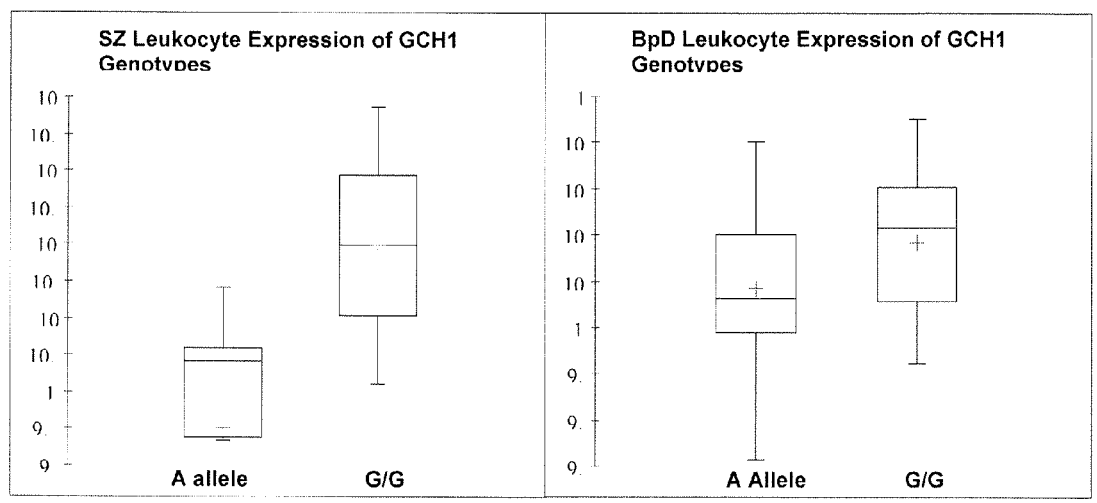
FIG. 6 is a graph illustrating leukocyte GCH1 expression in the SZ A allele group when compared to SZ and BpD GIG subjects.

Initial comparison of GCH1 leukocyte mRNA levels between SZ, BpD, and control subjects showed that GCH1 was downregulated in patient groups, which is consistent to that found in the CNS. SZ patients with the A allele has significantly lower plasma biopterin levels when compared to controls, while GIG SZ patients had similar levels to controls (and there were no differences between any of the control subject genotypes). As a result, differences in GCH1 transcript levels in A allele patients were tested as compared to GIG patients. Referring to FIG. 6, significantly lower leukocyte GCH1 expression was found in the SZ A allele group (n=12) when compared to SZ GIG subjects (n=7), which is consistent with plasma biopterin data obtained from this subject group. Data in FIG. 6 are natural log (ln) normalized via RMA, where the first panel illustrates GCH1 expression is significantly lower in peripheral leukocytes from A allele SZ patients compared to SZ GIG patients (p=0.024). The second panel of FIG. 6 illustrates that GCH1 expression is lower in A allele BpDpatients compared to GIG BpD patients (p=0.2). The box plots display the mean (+), median (horizontal line in box), first (Q1) and third (Q3) quartiles (ends of the boxes). Analysis of 17 BpD subjects also demonstrated lower levels of GCH1 in A allele carriers (n=9), when compared to GIG BpD patients (n=8), although this result was not significant.

Figure 7:
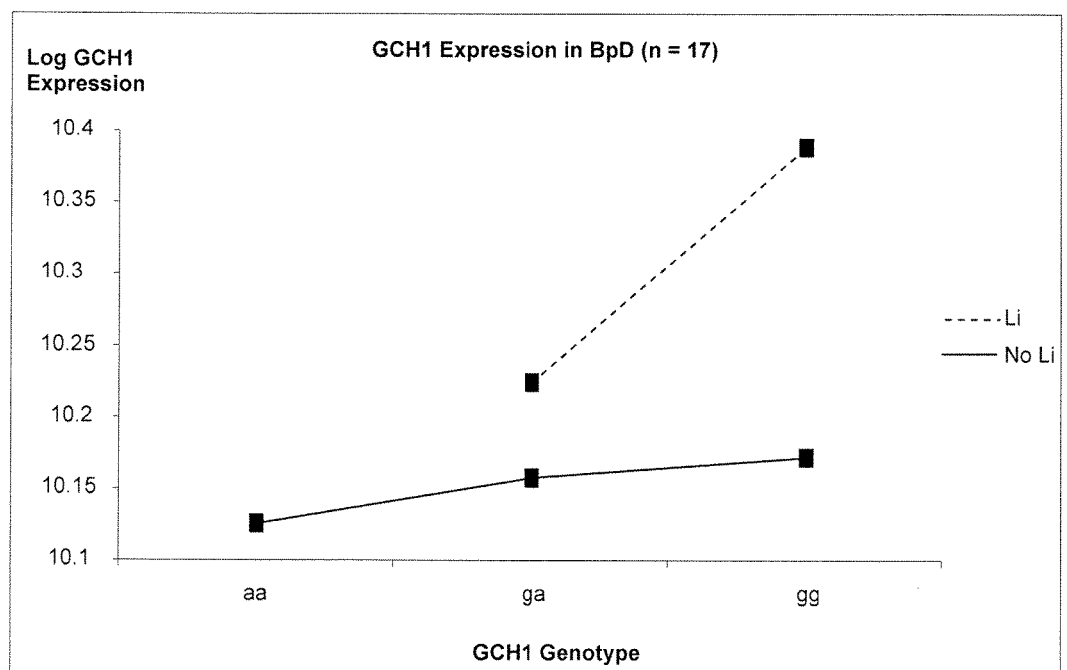
FIG. 7 is a graph illustrating leukocyte gene expression for BpD subjects.

Ten of the BpD subjects employed for this analysis had been treated with lithium, seven had not (16 of the 17 BpD subjects were also receiving neuroleptics). Subjects were therefore separated for both genotype and Li treatment groups, with the means calculated and plotted in FIG. 7, which illustrates mean log expression for BpD subjects without Li treatment (solid line) with the AA (n=2), A/G (n=4) and GIG (n=4) genotypes. Log mean expression for BpD subjects with Li treatment (dashed line) with the A/A (n=0), A/G (n=3) and GIG (n=4) genotypes. Although the results were not significant (likely due to small number in each group), the data was striking and consistent with all previous results, i.e., levels of GCH1 in the BpD Li untreated group (lowest in the A/A subjects and highest in the GIG BpD subjects) had a similar expression profile to the plasma biopterin levels in SZ subjects (see FIG. 4). In addition, subjects treated with Li had higher expression levels than subjects without Li treatment. Plasma biopterin levels show that Li-treatment likely increases plasma biopterin levels, which is likely accomplished via increased GCH1 expression.

The data thus suggests that subjects with the GCH1 BpD-associated genotype will have downregulated GCH1 mRNA (in both the periphery and CNS) that alters BH4 biosynthesis. The resultant BH4 deficit will thus contribute to BpD susceptibility, likely via altered CNS neurotransmission. The data also suggests that for Li treated patients, the biopterin deficit can be alleviated via increased GCH1 expression, which is supported by a similar GCH1 mRNA rise observed in the rat brain following Li-induced inositol depletion (via Li administration). Li has a major effect on plasma biopterin levels, thus suggesting that the increased biopterin levels in BpD subjects is due, in part, to Li upregulating GCH1 transcription and subsequently BH4 biosynthesis. Li treatment may thus be less effective in subjects with the BpD associated allele, and the data supports targeting of treatment for BpD based on GCH1 genotype.

With respect to the prediction of risk and/or screening, the present invention provides for the assay of GCH1 genotype for the presence of a GCH1 variant as a method for prediction of risk for SZ or SaD or a psychiatric disorder, neuropsychiatric disorder, or neurological disorder. The present invention also provides for the assay of GCH1 genotype for the presence of a GCH1 variant, in conjunction with the assay of BH4 system measures (e.g., plasma biopterin assay), as a method for prediction of risk and/or screening for SZ, SaD, or BpD, or other psychiatric disorders, neuropsychiatric disorders, or neurological disorders.

With respect to diagnosis, the present invention provide for the assay of GCH1 genotype for the presence of a GCH1 variant, in conjunction with the assay of BH4 system measures (e.g., plasma biopterin assay), as a method for diagnosis of SZ or SaD, or BpD or a psychiatric disorder, neuropsychiatric disorder, or neurological disorder. The present invention also provides for the assay of GCH1 genotype for the presence of a GCH1 variant, as a method for diagnosis of SZ or SaD, or other psychiatric disorders, neuropsychiatric disorders, or neurological disorders.

With respect to diagnosis incorporating symptoms, the present invention provides for the assay of GCH1 genotype for the presence of a GCH1 variant, in conjunction with assessment of specific symptoms and symptoms types, and in conjunction with the assay of BH4 system measures (e.g., plasma biopterin assay), as a method for diagnosis of SZ or SaD, or BpD or a psychiatric disorder or neuropsychiatric disorder, and/or the analysis of symptoms for those disorders. The present invention also provides for the assay of GCH1 genotype for the presence of a GCH1 variant, in conjunction with assessment of specific symptoms and symptoms types, as a method for diagnosis of SZ or SaD, or other psychiatric disorders, neuropsychiatric disorders, or neurological disorders.

With respect to prediction of prognosis, the present invention provides for the assay of GCH1 genotype for the presence of a GCH1 variant, in conjunction with the assay of BH4 system measures (e.g., plasma biopterin assay), as a method for prediction of prognosis of SZ or SaD, or BpD or a psychiatric disorder or neuropsychiatric disorder. The present invention also provides for the assay of GCH1 genotype for the presence of a GCH1 variant as a method for prediction of prognosis of SZ or SaD, or other psychiatric disorders, neuropsychiatric disorders, or neurological disorders.

With respect to the assessment of patient treatment benefit, the present invention provides for the assay of GCH1 genotype for the presence of a GCH1 variant, in conjunction with the assay of BH4 system measures (e.g., plasma biopterin assay), as a method for defining those patients with a psychiatric disorder, neuropsychiatric disorder, or neurological disorder (e.g., SZ, SaD, BpD) who would benefit from treatment designed to normalize their BH4 system levels, or prevent a potential biopterin or BH4 system deficit in those at-risk. The present invention also provides for the assay of GCH1 genotype for the presence of a GCH1 variant, as a method for defining those patients with a psychiatric disorder, neuropsychiatric disorder, or neurological disorder (e.g., SZ, SaD, BpD) who would benefit from treatment designed to normalize their BH4 system levels and/or improve their symptoms.

With respect to defining at-risk subjects, the present invention provides for the assay of GCH1 genotype for the presence of a GCH1 variant as a method for defining those at risk for SZ or SaD or other psychiatric, neuropsychiatric, or neurological disorder. The present invention also provides for the assay of GCH1 genotype for the presence of a GCH1 variant, in conjunction with the assay of BH4 system measures (e.g., plasma biopterin assay), as a method for defining those at risk for SZ, SaD, or BpD, or other psychiatric disorders, neuropsychiatric disorders, or neurological disorders.

With respect to defining at-risk subjects who would benefit from prophylactic treatment, the present invention provides for the assay of GCH1 genotype for the presence of a GCH1 variant, in conjunction with the assay of BH4 system measures, as a method for defining those at risk for development of SZ or SaD or BpD or a psychiatric disorder, neuropsychiatric disorder, or neurological disorder who would benefit from treatment designed to normalize their BH4 system levels and/or improve their symptoms. The present invention also provides for the assay of GCH1 genotype for the presence of a GCH1 variant as a method for defining those at risk for development of a psychiatric, neuropsychiatric or neurological disorders, including SZ or SaD, and those who would benefit from useful treatments designed to normalize or improve their BH4 system levels, improve their symptoms, and/or benefit from Li, neuroleptic(s), and/or other antipsychotic or mood stabilizers, and/or treatments (e.g., administration of electrical stimulation and/or electroconvulsive therapy (ECT), transcranial magnetic stimulation (TMS), electrical brain stimulation, deep brain stimulation, and/or inositol depletion treatments).

With respect to the treatment and prevention of disorders, the present invention provides for the treatment of subjects with, or who are at risk of developing, SZ or SaD and/or a psychiatric disorder, neuropsychiatric or neurological disorder, who either carry a GCH1 variant and/or a BH4 system gene variant and/or a variant in another gene that can lead to BH4 system deficit or alteration, or who have (or are at risk for developing) a fasting or non-fasting biopterin level (e.g. plasma biopterins) and/or BH4 and/or pterin levels, and/or GCH1 RNA and/or GTPCH protein that lie in the range defined as "low" or "altered" or is different from the mean (or median, mode, normal range, expected value, etc.) compared to controls, by treatment with useful treatments. Treatments will be used as a way to boost and/or alter BH4 levels, biopterin levels, and/or affected BH4 system component levels in those in need of BH4 system supplementation and/or normalization, with and/or at-risk of developing a disorder. Such treatment(s) can be used either alone or in conjunction with other "useful treatments" which include, but are not limited to: treatment with pterin(s) and/or other molecules, including BH4 and/or biopterin and/or dihydrobiopterin and/or sepiapterin and/or sapropterin dihydrochloride. Other medications that may improve BH4 system status or that can be used in conjunction with such treatments may include neuroleptic or other psychotropic medications (e.g., Phenothiazines, Chlorpromazine, Fluphenazine, Perphenazine, Prochlorperazine, Thioridazine, Trifluoperazine, Butyrophenones, Haloperidol, Droperidol, Pimozide, Clozapine, Olanzapine, Risperidone, Quetiapine, Ziprasidone, Aripiprazole, Bifeprunox; norclozapine (ACP-104), Symbyax, Tetrabenazine, and lithium), ECT, TMS, and other like medications. Such treatment(s) may be provided to those with SZ, SaD, BpD, or BH4-responsive PKU, hyperphenylalanenemia (Phe and/or aspartame and/or Phe-containing polypeptides will not be used for hyperphenylalaninemia), and/or dystonias. Such treatments will also be used for other psychiatric and/or neuropsychiatric disorders and/or neurological disorders.

With respect to the treatment of patients with useful treatments designed or used to normalize BH4 and/or BH4 system levels, the present invention also provides for the treatment of SZ, SaD, or BpD who carry a GCH1 variant (or a BH4 system gene variant), in conjunction with a fasting or non-fasting biopterins (e.g., plasma biopterins), BH4, BH4 system measures, pterin levels, GCH1 RNA and/or GTPCH protein, that lie in the range defined as "low" or "altered" compared to controls, with therapeutic amounts of useful treatments. The present invention also provides for the treatment of SZ, SaD, or BpD (or other psychiatric disorders, neuropsychiatric disorders, or neurological disorders in need of treatment), in subjects who carry a GCH1 gene (or a BH4 system gene) variant, by treatment with therapeutic amounts of useful treatments. It should also be recognized by those of skill in the art that the present invention may be used to determine the presence of a GCH1 G/G genotype, and any BH4 system surplus, such as high BH4 and/or bopterin, that may factor into diseases symptoms, disease risk, and/or the applicable treatment response.

With respect to the treatment of at-risk subjects with useful treatments designed or used to normalize BH4, the present invention provides for the treatment of those at risk of developing SZ, SaD, or BpD, or other psychiatric disorders or neuropsychiatric disorders or neurological disorders (or other disorders in need of treatment) who carry a GCH1 variant (or a BH4 system gene variant) in conjunction a "low" or "altered" BH4 system and/or with a fasting or non-fasting biopterin levels (e.g., plasma biopterins), BH4 levels, and/or pterin levels, as well as GCH1 RNA and/or GTPCH proteins that lie in the range defined as "low" or "altered" or is different from the mean (or median, mode, normal range, expected value(s) etc.) compared to controls and/or other patient groups, by treatment with useful treatments. The present invention also provides for the treatment of those at risk of developing SZ or SaD or BpD (or other disorders in need of treatment) who carry a GCH1 variant (or a BH4 system gene variant), by treatment with useful treatments. Subjects determined to be at-risk for development of a psychiatric, neuropsychiatric or neurological disorders can include gametes, embryos, and/or fetuses, and assessment of risk status can be made from parental and/or prenatal testing.

With respect to prevention and/or treatment using gene or protein therapies, the present invention provides for the treatment of those with, or at risk of developing, SZ or SaD or a psychiatric, neuropsychiatric, or neurological disorder (or other disorders in need of treatment) who carry a GCH1 variant (or a BH4 system gene variant), either alone or in conjunction with a fasting or non-fasting biopterins (e.g. plasma biopterins) and/or BH4 and/or pterin levels, and/or GCH1 RNA and/or GTPCH protein that lie in the range defined as "low" or "altered" or different from the mean (or median, mode, normal range, expected value, etc.) compared to controls, by treatment with therapeutic DNA and/or RNA molecules to cells, tissues, or organs, or locally or systemically (including injection, intravenously, orally, suppository, intranasally, intracerebrally, intrathecal, parenterally, or by infusion), or by administration to isolated cells, tissues, organs, fluids, etc. Therapeutic DNA and/or RNA molecules include, but are not limited to, sequences related to those of GCH1 (such as for example sequence containing the −959 nt G to A: rs10137071, "G" allele), other BH4 system genes, and/or related genes, and can be introduced by using vectors, viral particles, capsules, liposomes, and other containers or delivery methods, or by binding to other molecules or particles, surfaces, or materials. Therapeutic DNA and/or RNA molecules can also be introduced to sperm, eggs, embryos, fetuses, stem cells, or other cells. Additionally, in conjunction with these procedures, one or more other useful treatments may also be used.

With respect to imaging correlates in the screening, detection, diagnosis, prognosis, definition of at-risk, and assessment of treatment response, the present invention provides for the assay of GCH1 genotype (or assay of a BH4 system gene variant), altered biopterin level, and/or BH4 system measures (e.g., biopterin), for those with or at risk of developing a psychiatric, neuropsychiatric, or neurological disorder or other disorder, and the determination use of MRI, MRS, fMRI, PET, SPECT, CT, or other imaging technologies and methods to assess CNS, peripheral, structural, biochemical activity, physiological, and/or other differences or changes in subjects.

With respect to gene or protein expression in the screening, detection, diagnosis, prognosis, definition of at-risk, and assessment of treatment response, the present invention provides for the assay of GCH1 genotype (or of a detected BH4 system gene variant) and/or assay of the BH4 system or BH4 system measures, for those with or at risk of developing a psychiatric, neuropsychiatric, or neurological disorder, and the use of any RNA (including miRNA) and/or protein and/or peptide expression measurement, such as microarray analysis, mass spectrometry analysis, protein microarray analysis or electrophoresis analysis, and can be used for disease and/or symptom detection, diagnosis, prognosis, definition of at-risk, determination of treatment, assessment of treatment response. Expression analysis in any tissue, and/or organs and/or cells, from a subject or animal model could be employed. Expression measurements, profiling, and detection methods are included to assess CNS, peripheral, structural, biochemical activity, physiological, and/or other differences or changes in subjects.

With respect to the detection, diagnosis and medication of subjects having BH4 system gene mutations and variants and alterations, the present invention provides for the screening, determination of at-risk, detection, diagnosis, prognosis, determination of treatment and treatment of disorders, including whether there is a genetic or epigenetic (e.g., methylation, acetylation, and/or ubiquitylation) difference affecting the gene(s), as well as their promoters, enhancers, suppressors and other regulatory regions, regulatory RNAs (such as miRNAs), such as whether there is a nucleotide variant (e.g., a G/A nucleotide substitution or a nucleotide deletion), or copy number polymorphism and/or duplication, deletion or other mutation or change, whether newly detected or previously known, such as for GCH1, NURR1, GSK (including GSK 3 beta and alpha), IMPase, AKT1, AKT/PKB, AKT2, AKT3 or IPP mutations and variants, and for other BH4 system genes.

With respect to the generation of, and/or breeding with, and/or use of a GCH1 transgenic animal model and/or animal model with a targeted disruption of the GCH1 gene, the present invention provides for research into the etiology and pathogenesis of, as well as the development of mediations and treatments, for neuropsychiatric, and neurological disorders, including SZ, SaD and BpD.

What is claimed is:

1. A method of treating a human subject for schizophrenia or schizoaffective disorder, comprising the steps of:
    obtaining a blood sample from the subject;
    amplifying a genomic region spanning G/A genotype at −959 nt of GCH1;
    detecting an A allele at position −959 nt of GCH1 in the sample;
    detecting decreased levels of a biopterin marker in the sample; and
    administering a therapeutic amount of a BH4 supplement to the subject with an A allele at position −959 nt of GCH1 and decreased biopertin marker levels to treat the subject for schizophrenia or schizoaffective disorder.

2. The method of claim 1, wherein the BH4 supplement is sapropterin dihydrochloride.

* * * * *

SEQUENCE LISTING

```
<160> NUMBER OF SEQ ID NOS: 4

<210> SEQ ID NO 1
<211> LENGTH: 351
<212> TYPE: DNA
<213> ORGANISM: Homo sapiens

<400> SEQUENCE: 1
tcaagtgagg aaaaaggtcc atttattaat ctcaaagaaa acagttacag cagatgtcac      60
tggttaagag ttcagttggt gaatagcatt tcacaatttg taccaacatc tggggaaaga     120
cgctttgcat ggaactgtaa aacaattgag caccaaatct gcacaactgc gtttatagaa     180
aatgcgatgg gttttataga gatgaggtct tgctatgttt ccaggctgg tctcgaactc      240 ttggcctcaa gcgatcctcc cgcctcggtc tccccaagcg ccgggagtac aggcgtgagc     300
caccgacgga aatggatttt aagtgaaagt cctatcttcg tttgcaaatc a              351

<210> SEQ ID NO 2
<211> LENGTH: 351
<212> TYPE: DNA
<213> ORGANISM: Homo sapiens

<400> SEQUENCE: 2
tcaagtgagg aaaaaggtcc atttattaat ctcaaagaaa acagttacag cagatgtcac      60
tggttaagag ttcagttggt gaatagcatt tcacaatttg taccaacatc tggggaaaga     120
cgctttgcat ggaactgtaa aacaattgag caccaaatct gcacaactgc gtttatagaa     180
aatgcaatgg gttttataga gatgaggtct tgctatgttt ccaggctgg tctcgaactc      240 ttggcctcaa gcgatcctcc cgcctcggtc tccccaagcg ccgggagtac aggcgtgagc     300
caccgacgga aatggatttt aagtgaaagt cctatcttcg tttgcaaatc a              351

<210> SEQ ID NO 3
<211> LENGTH: 21
<212> TYPE: DNA
<213> ORGANISM: Artificial Sequence
<220> FEATURE:
<223> OTHER INFORMATION: Forward primer for identifying allele

<400> SEQUENCE: 3
tcaagtgagg aaaaaggtcc a                                                21

<210> SEQ ID NO 4
<211> LENGTH: 22
<212> TYPE: DNA
<213> ORGANISM: Artificial Sequence
<220> FEATURE:
<223> OTHER INFORMATION: Reverse primer for identifying allele

<400> SEQUENCE: 4
tgatttgcaa acgaagatag ga                                               22
```